United States Patent
Hunt et al.

(10) Patent No.: US 7,670,323 B2
(45) Date of Patent: *Mar. 2, 2010

(54) PORTABLE WOUND TREATMENT APPARATUS HAVING PRESSURE FEEDBACK CAPABILITIES

(75) Inventors: Kenneth William Hunt, Wimbourne (GB); Keith Patrick Heaton, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/713,485

(22) Filed: Mar. 2, 2007

(65) Prior Publication Data

US 2007/0167927 A1 Jul. 19, 2007

Related U.S. Application Data

(63) Continuation of application No. 09/613,497, filed on Jul. 11, 2000, which is a continuation of application No. 09/078,223, filed on May 13, 1998, now Pat. No. 6,142,982.

(51) Int. Cl.
*A61M 1/00* (2006.01)

(52) U.S. Cl. .................. 604/313; 604/35; 604/305; 604/306; 604/307; 604/308; 604/317; 604/318; 604/319; 604/320; 604/321; 604/322; 604/323; 604/540; 604/541; 604/542; 604/544; 604/902; 600/131

(58) Field of Classification Search ............... 604/319, 604/316, 305, 541, 315, 543
See application file for complete search history.

(56) References Cited

U.S. PATENT DOCUMENTS

| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |

(Continued)

FOREIGN PATENT DOCUMENTS

AU 550575 A1 8/1982

(Continued)

OTHER PUBLICATIONS

Chariker, Mark E., M.D., et al; Effective management of incisional and cutaneous fistulae with closed suction wound drainage; Contemporary Surgery/vol. 34, Jun. 1989 pp. 59-63.

(Continued)

*Primary Examiner*—Tatyana Zalukaeva
*Assistant Examiner*—Ilya Y Treyger

(57) ABSTRACT

A reduced pressure treatment apparatus includes a drape for positioning over the wound site to create and maintain a substantially air-tight cavity between the wound site and the drape. A multi-lumen suction tube is provided to be attached to a reduced pressure source. The multi-lumen suction tube includes a center lumen and at least one outer lumen and is configured to deliver reduced pressure beneath the drape to the substantially air-tight cavity. The multi-lumen suction tube is adapted to allow fluid to be drawn from the wound site through the center lumen and pressure to be monitored at the wound site through the at least one outer lumen.

29 Claims, 5 Drawing Sheets

U.S. PATENT DOCUMENTS

| | | | |
|---|---|---|---|
| 3,066,672 A | 12/1962 | Crosby, Jr., et al. | |
| 3,089,492 A | 5/1963 | Owens | |
| 3,142,298 A | 7/1964 | Koski et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,360 A | 4/1981 | Perez | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,342,745 A | 8/1982 | Mirkovitch | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,406,656 A * | 9/1983 | Hattler et al. | 604/523 |
| 4,419,097 A | 12/1983 | Rowland | |
| 4,444,545 A | 4/1984 | Sanders et al. | |
| 4,465,485 A | 8/1984 | Kashmer et al. | |
| 4,468,219 A | 8/1984 | George et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,534,356 A * | 8/1985 | Papadakis | 600/358 |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,795,435 A | 1/1989 | Steer | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,930,997 A | 6/1990 | Bennett | |
| 4,941,882 A | 7/1990 | Ward et al. | |
| 4,953,565 A | 9/1990 | Tachibana et al. | |
| 4,969,880 A | 11/1990 | Zamierowski | |
| 4,979,944 A * | 12/1990 | Luzsicza | 604/118 |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,260,066 A | 11/1993 | Wood et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,449,347 A | 9/1995 | Preen et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A * | 6/1997 | Argenta et al. | 128/897 |
| 5,645,081 A | 7/1997 | Argenta et al. | |
| 5,678,564 A | 10/1997 | Lawrence et al. | |
| 5,776,119 A | 7/1998 | Bilbo et al. | |
| 5,827,246 A | 10/1998 | Bowen | |
| 6,071,267 A | 6/2000 | Zamierowski | |
| 6,135,116 A | 10/2000 | Vogel et al. | |
| 6,142,982 A | 11/2000 | Hunt | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,458,109 B1 * | 10/2002 | Henley et al. | 604/304 |
| 6,471,982 B1 * | 10/2002 | Lydon et al. | 424/443 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,316,672 B1 | 1/2008 | Hunt | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |

FOREIGN PATENT DOCUMENTS

| | | | |
|---|---|---|---|
| AU | 745271 | 4/1999 | |
| AU | 755496 | 2/2002 | |
| CA | 2005436 | 6/1990 | |
| DE | 26 40 413 A1 | 3/1978 | |
| DE | 43 06 478 A1 | 9/1994 | |
| DE | 295 04 378 U1 | 10/1995 | |
| EP | 0080179 A1 | 6/1983 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 0619105 A1 | 10/1994 | |
| EP | 1018967 B1 | 8/2004 | |
| GB | 692578 | 6/1953 | |
| GB | 1579860 | 11/1980 | |
| GB | 2125296 A * | 3/1984 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2277035 A | 10/1994 | |
| GB | 2 333 965 A | 8/1999 | |
| GB | 2 329 127 B | 8/2000 | |
| JP | 56500360 T | 3/1981 | |

| | | |
|---|---|---|
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO95/17912 | 7/1995 |
| WO | WO 96/05873 | 2/1996 |
| WO | WO 97/18007 | 5/1997 |
| WO | WO 99/13793 | 3/1999 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61(1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51(3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999 .
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu: A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, May 2, 1986, pp. 42-46, and 7 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
N.A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksary , U.S.S.R. 1986) pp. 94-96.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinović, V. Dukić, Ž. Maksimović, D. Radak, and P. Peška, "Vacuum Therapy in the Treatment of Peripheral Blood Vessels," Timok Medical Journal 11 (1986), pp. 161-164.
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64,90-96, 167-170, and 210-211.
Quayle Office Action dated Nov. 16, 2001 for U.S. Appl. No. 09/613,497.
Response filed Mar. 19, 2004 to Quayle Office Action dated Nov. 16, 2001 for U.S. Appl. No. 09/613,497.
Non-Final Office Action dated Jul. 13, 2004 for U.S. Appl. No. 09/613,497.
Response filed Jan. 12, 2005 to Non-Final Office Action dated Jul. 13, 2004 for U.S. Appl. No. 09/613,497.
Non-Final Office Action dated Feb. 7, 2006 for U.S. Appl. No. 09/613,497.
Response filed Jul. 08, 2006 to Non-Final Office Action dated Feb. 7, 2006 for U.S. Appl. No. 09/613,497.
Notice of Non-Compliant dated Jul. 14, 2006 for U.S. Apppl. No. 09/613,497.
Response filed Aug. 10, 2006 to Non-Compliant dated Jul. 14, 2006 for U.S. Appl. No. 09/613,497.
Notice of Allowance and Fee(s) Due dated Oct. 13, 2006 for U.S. Appl. No. 09/613,497.
Request for Continued Examination dated Feb. 26, 2007 for U.S. Appl. No. 09/613,497.
Notice of Allowance and Fee(s) Due dated Apr. 5, 2007 for U.S. Appl. No. 09/613,497.
Request for Continued Examination dated Jul. 9, 2007 for U.S. Appl. No. 09/613,497.
Response filed Jul. 19, 2007 to Interview Summary Jul. 19, 2007 for U.S. Appl. No. 09/613,497.
Notice of Allowance and Fee(s) Due dated Aug. 6, 2007 for U.S. Appl. No. 09/613,497.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

* cited by examiner

PORTABLE WOUND TREATMENT APPARATUS HAVING PRESSURE FEEDBACK CAPABILITIES

CROSS-REFERENCE TO RELATED APPLICATION

This application is a continuation application of U.S. patent application Ser. No. 09/613,497, filed Jul. 11, 2000, which is a continuation of U.S. patent application Ser. No. 09/078,223, filed May 13, 1998, now U.S. Pat. No. 6,142,982, which is a continuation of International Application No. PCT/GB96/02802, filed Nov. 14, 1996, which claims priority to British Patent Application No. GB9523253.4, filed Nov. 14, 1995. All of the above-mentioned patents and applications are hereby incorporated by reference in their entirety.

BACKGROUND OF THE INVENTION

This invention relates to the healing of wounds and, more particularly, to apparatus for stimulating the healing of superficial wounds.

PCT Application No. GB95/01983 (WO 96/05873) describes apparatus for stimulating the healing of wounds comprising a porous pad which is permeable to fluids for introduction into the wound, a dressing for covering the wound and providing an air-tight seal around the wound, a drainage tube connecting the pad to a suction pump so that negative pressure can be applied to the wound to draw fluids therefrom, and a canister for collecting fluids sucked from the wound. The apparatus described in the above application has proved to be clinically effective but there are some limitations in its use.

The apparatus described in the above PCT application is effective for treating a wide variety of different types and sizes of wounds. However, it may require the patient to undergo treatment on the apparatus for a long period. In cases where the patient is confined to bed this may not be a major problem but where the patient is mobile it means that he or she would be confined for long periods while the treatment takes place.

SUMMARY OF THE INVENTION

According to one aspect of the present invention there is provided a portable therapeutic apparatus for stimulating the healing of superficial wounds in a person, which comprises a housing containing a suction pump and a canister for containing fluids drawn from the wound by said pump, said canister including means for connection to a dressing in the region of the wound and a harness or belt for supporting the housing on the person.

Typically, the housing will have a curved surface on the side intended to be supported against the person's body so as to make the apparatus more comfortable to wear. In addition, controls and indicators indicating the status of the treatment being applied to the wound are preferably located on the upper side of the housing so that the patient can easily see, e.g. the level of suction pressure being applied and the programme for such treatment.

The suction pump is conveniently driven by an electric motor and batteries for such motor may be contained within the housing. However, it is generally more convenient to provide a separate housing for the batteries since these can be placed on the belt or harness in such a way as to balance the weight of the housing, preferably in a housing shaped similarly to the housing for the pump and canister.

The canister should be removably mounted within the housing, e.g. by means of a latch or similar release mechanism, so that the canister can be readily removed and replaced when full.

In a portable therapeutic apparatus (in contrast with a static apparatus of the kind described in the above PCT application which cannot be easily carried by the patient), it is less easy to determine the pressure prevailing at the wound site being treated. This is because the pressure will depend, in part, upon the hydrostatic height between the pump and the wound being treated and this height may vary during the treatment, depending upon the patient's movements. Apparatus in accordance with the invention overcomes this problem by providing an additional conduit connecting the wound site or an area close thereto to a pressure-detecting means, preferably located in the housing. The pressure-detecting means can be linked to a microprocessor programmed to maintain such pressure within a predetermined range irrespective of the movement of the patient. This can be done by, for example, signaling the pump to increase its speed where the hydrostatic pressure increases between the pump and the wound site or, conversely, reducing its speed where the hydrostatic pressure is reduced. This feature can also be used in a static therapeutic apparatus of the kind described in the abovementioned PCT application.

In the apparatus described in the above PCT application, the level of liquid in the canister is monitored by capacitance measurement. It has now been found that a simpler way of determining when the canister is filled is by measuring or detecting the pressure drop across the canister. The pressure drop can be increased by providing a filter barrier in the region of the outlet end of the canister.

Thus, when the liquid reaches a level within the canister so as to substantially occlude the filter, a sharp pressure change occurs in the conduit between the canister and the pump. By monitoring this pressure change, the point at which the canister is filled can be accurately determined.

Other features which are considered as characteristic for the invention are set forth in the appended claims.

Although the invention is illustrated and described herein as embodied in a title of invention, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 2A:
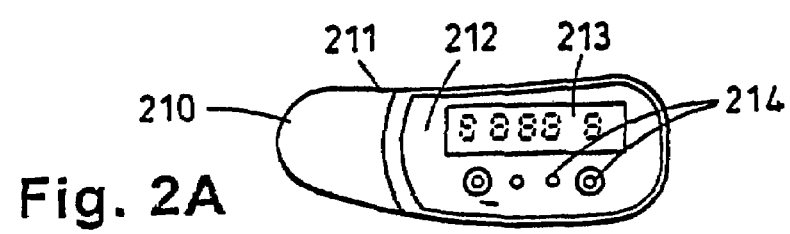
FIGS. 2A and B are pictorial representations of the housing of the pump and canister, FIGS. 3A and B are pictorial representations of the apparatus supported on a belt and harness respectively.
Figure 2B:
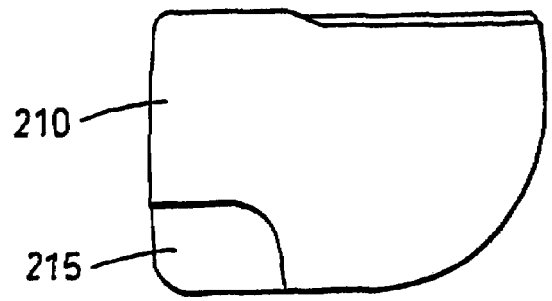

Referring to the drawings, the portable therapeutic apparatus comprises a housing 210 (best shown in FIGS. 2A and 2B), having rounded corners and a side 211 which is concavely curved in order to fit comfortably to the wearer's body.

The shaping of the housing with curved surfaces is to avoid sharp corners or edges which could dig in to the user or his career. The upper surface 212 is generally flat and has an LCD screen 213 on which details such as applied pressure can be displayed. Control buttons 214 are provided to adjust pressures and treatment intervals. Provision is made for housing a canister within the housing and a snap release cover 215 is arranged for removing or introducing the canister.

Figure 3A:
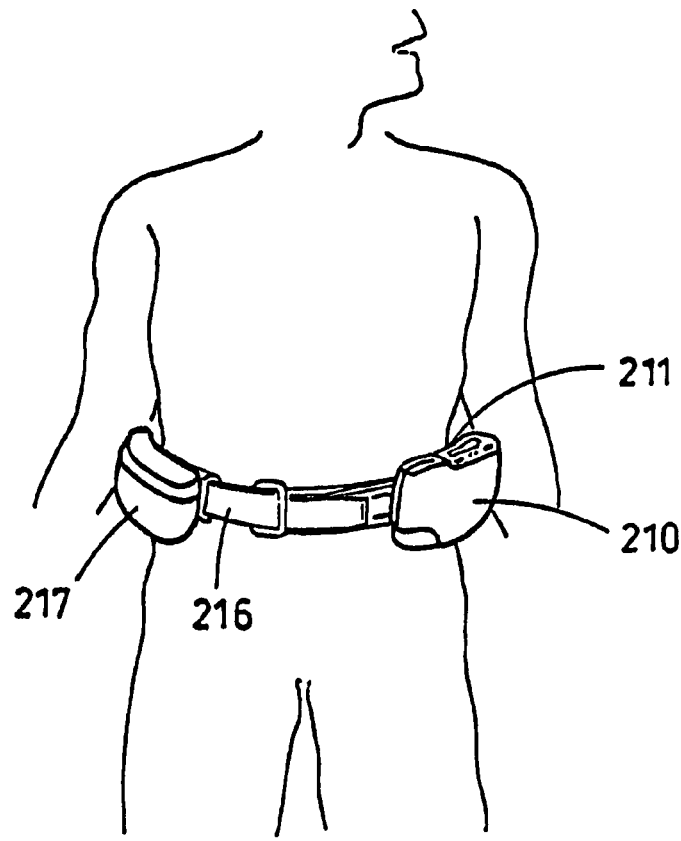
Figure 3B:
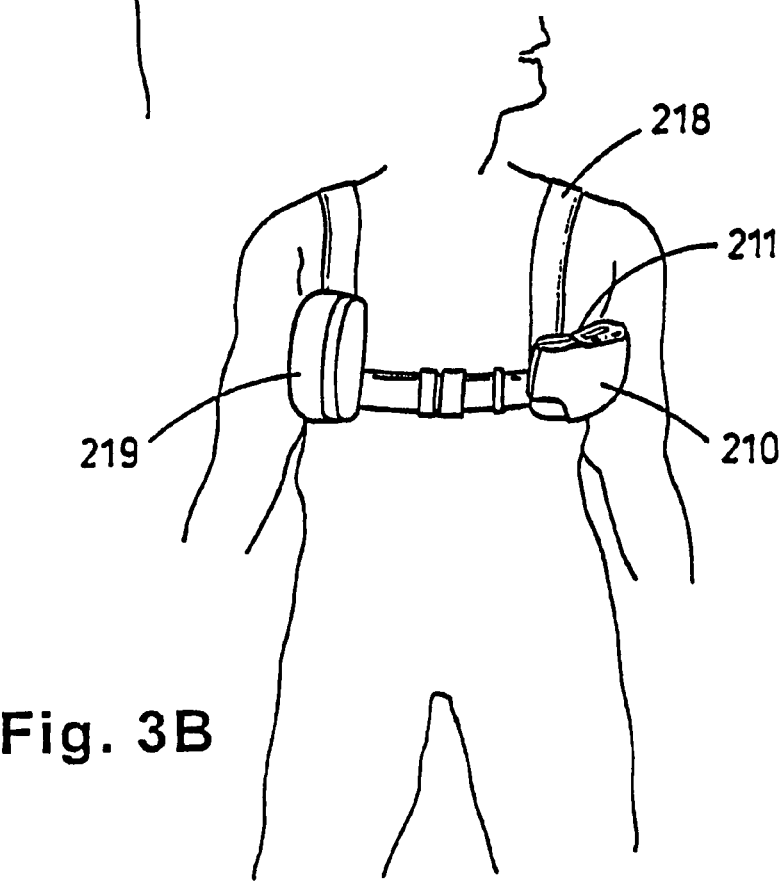

FIGS. 3A and 3B show schematically ways in which the housing 210 may be supported on the patient's body. In FIG. 3A the housing 210 is supported on a belt 216 and its weight is balanced by a similarly rounded casing 217 containing a rechargeable battery pack. FIG. 3B shows an alternative arrangement in which the housing is supported on a harness 218 and again a battery pack is contained in a housing 219, also supported on the harness.

Figure 4:
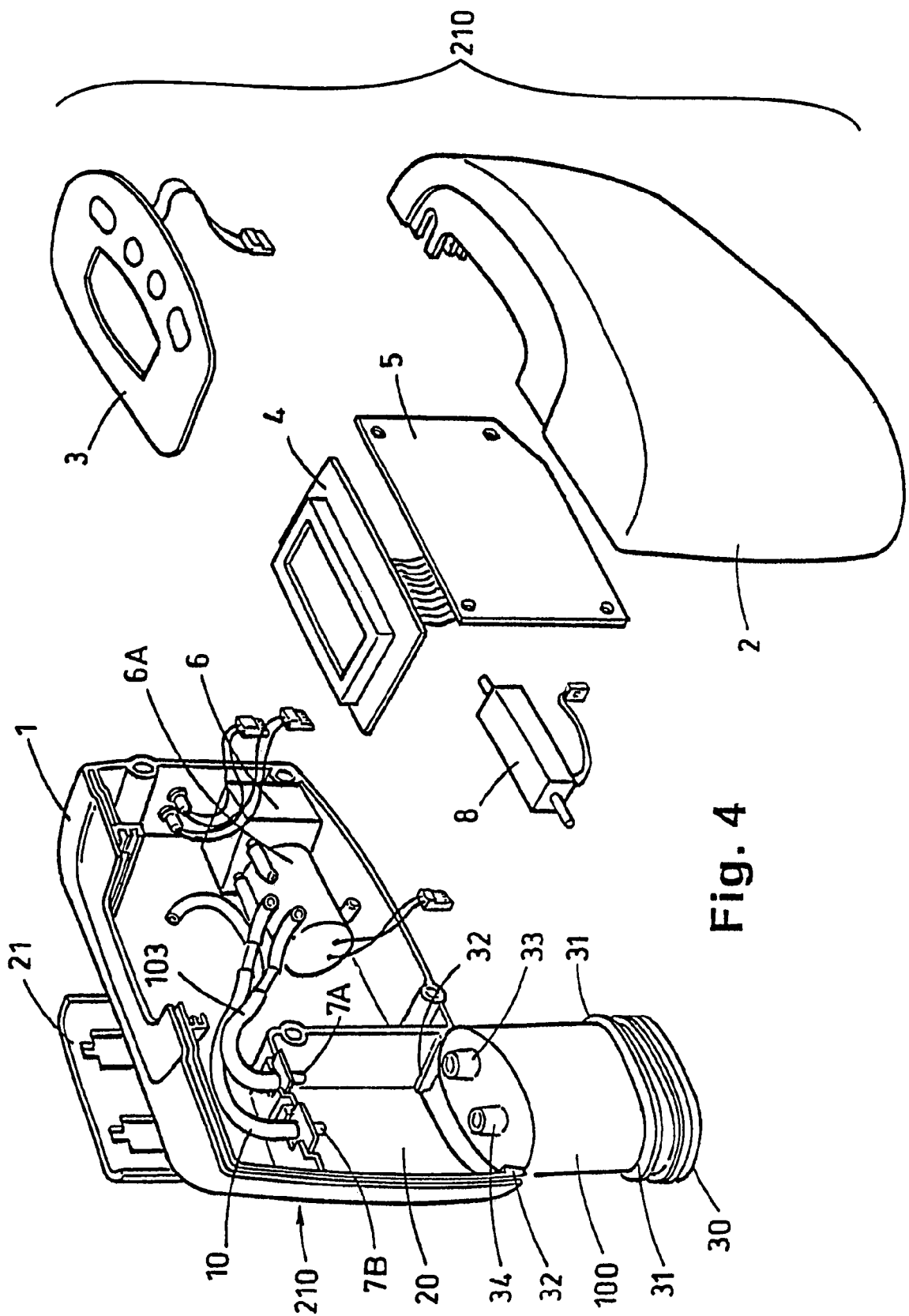
FIG. 4 is an exploded view of the housing showing the contents.

FIG. 4 shows an exploded view of the housing 210 indicating the main components within the housing. The housing consists of front and rear shell mouldings 1 and 2 having an external belt clip 21 for attachment to a belt or harness.

Within housing shell 1 is located a suction pump 6 with associated electric motor 6A and the pump is connected by a silicon rubber tube 103 to a canister spigot 7A in a cavity 20 for the canister 100. Also connected to a second canister spigot 7B via a tube 10 is a pressure relief valve 8 and both tubes 103 and 10 are connected via T-connectors T to pressure transducers (not shown). A microprocessor 4 is mounted on a PCB board 5 and a membrane assembly 3 incorporates an LCD indicator and control buttons.

The apparatus may include means for recording pressures and treatment conditions given to a particular patient which may be printed out subsequently by the physician. Alternatively, the equipment may include a modem and a telephone jack so that the conditions under which the patient has been treated can be interrogated by the physician from a distant station.

Canister 100 is a push fit into the cavity 20 and its lower end is supported in a cover 30. The cover 30 incorporates fingers 31 which are releasably engageable with lips 32 to hold the canister in position. The canister and the latch mechanism is arranged so that when the latch is engaged, the spigots 7A and 7B are in sealing engagement or abutment with tubular protrusions 33 and 34 formed in the top of the canister.

Figure 1:
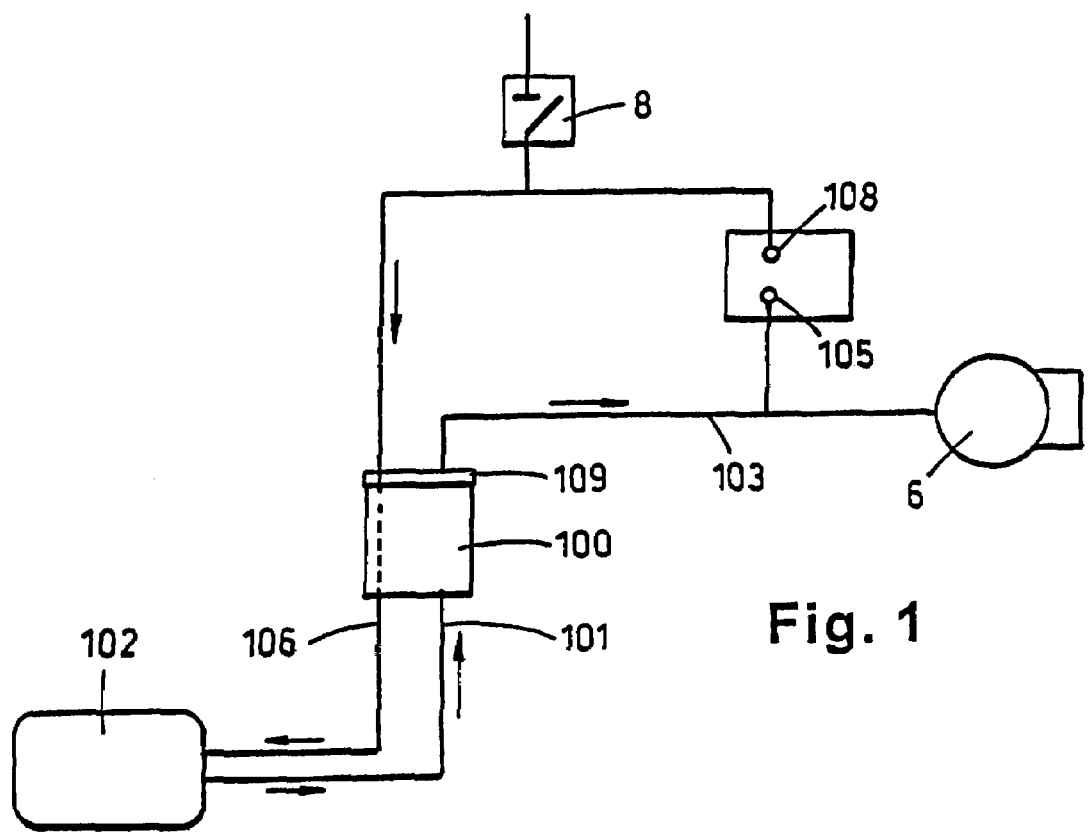
FIG. 1 is a schematic layout of the apparatus in accordance with the invention.

The method of operation of the apparatus can be appreciated from the schematic layout in FIG. 1, in which the canister 100 is connected via tube 101 to a porous dressing 102 at the wound site. Suction is applied to the wound site via the canister by a tube 103, connected to the pump 6. The pressure in the tube 103 is detected by the transducer 105.

A second tube 106 is connected to the wound site 102 at one end, and also to a pressure relief valve 8 and to a second transducer 108. Tubes 106 and 101 can be combined in a multi-partitioned tube in manner to be described later. By means of tube 106 and transducer 108 the pressure at the wound site can be measured or monitored. A filter 109 is placed at or close to the outlet end of the canister 100 to prevent liquid or solid particles from entering the tube 103. The filter is a bacterial filter which is hydrophobic and preferably also lypophobic.

Thus, aqueous and oily liquids will bead on the surface of the filter. During normal use there is sufficient air flow through the filter such that the pressure drop across the filter is not substantial.

As soon as the liquid in the canister reaches a level where the filter is occluded, a much increased negative pressure occurs in tube 103 and this is detected by transducer 105. Transducer 105 is connected to circuitry which interprets such a pressure change as a filled canister and signals this by means of a message on the LCD and/or buzzer that the canister requires replacement. It may also automatically shut off the working of the pump.

In the event that it is desired to apply intermittent suction to the wound site, a pressure relief valve 8 enables the pressure at the wound site to be brought to atmospheric pressure rapidly. Thus, if the apparatus is programmed, for example, to relieve pressure at 10 minute intervals, at these intervals valve 8 will open for a specified period, allow the pressure to equalize at the wound site and then close to restore the suction. It will be appreciated that when constant suction (or negative pressure) is being applied to the wound site, valve 8 remains closed and there is no leakage from atmosphere. In this state, it is possible to maintain negative pressure at the wound site without running the pump continuously, but only from time to time, to maintain a desired level of negative pressure (i.e. a desired pressure below atmospheric), which is detected by the transducer 105. This saves power and enables the appliance to operate for long periods on its battery power supply.

Instead of running two separate tubes to the wound site, it is preferable to contain tubes 106 and 101 in a single tube which is connected through the canister.

Thus, for example, tubes 103 and 101 may comprise an internal tube surrounded by an annular space represented by tube 106. This is illustrated in FIGS. 5A to 5F and in a modified form in FIG. 6E.

Figure 6A:
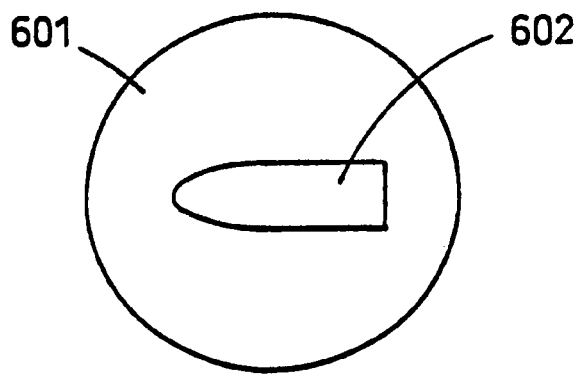
FIGS. 6A to D show various views of a foam dressing connector for connecting the housing to the dressing.
Figure 6B:
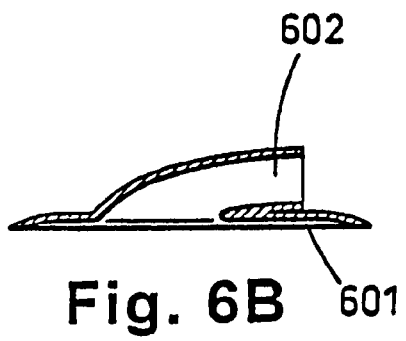
Figure 6C:
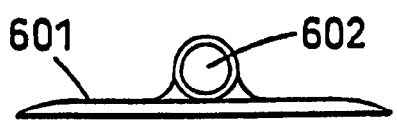
Figure 6D:
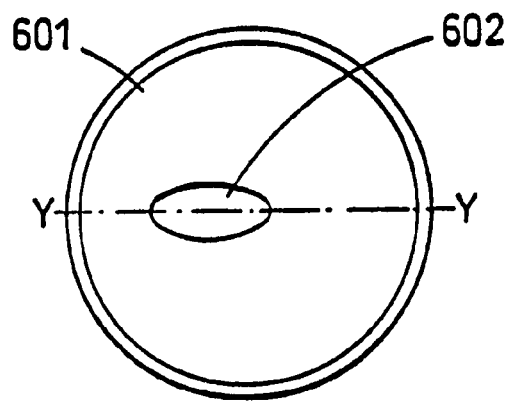
Figure 6E:
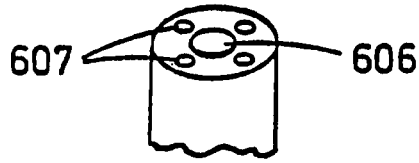
FIG. 6E shows a section of a modified multi-lumen tube.

In an alternative embodiment, the multi-lumen tube may be constructed as shown in FIG. 6E. In this embodiment, the internal bore 606 comprises the line 101 (see FIG. 1) and is used to extract fluids from the wound site. Air flow (represented by line 106 in FIG. 1) passes down conduits 607 located within the walls of the tube. By spacing the conduits 607 at 90" intervals around the tube, the risk of arresting the air flow by kinking or twisting the multi-lumen tube is minimized.

Figure 5A:
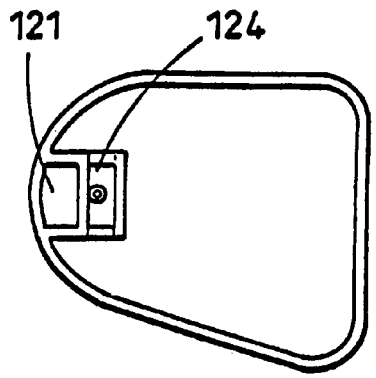
FIGS. 5A to F show various views of a preferred form of the canister and a section of a multi-lumen tube.
Figure 5D:
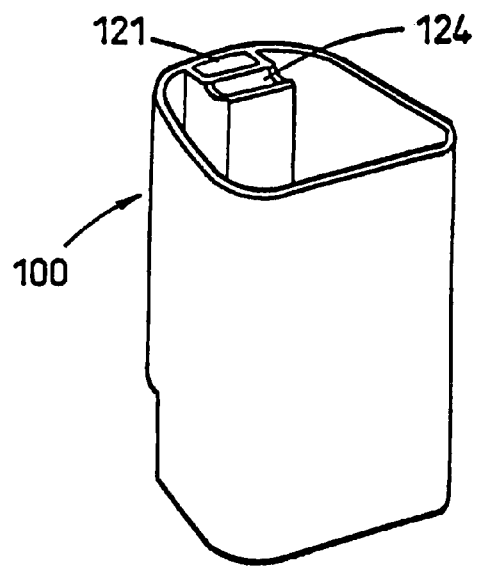
Figure 5B:
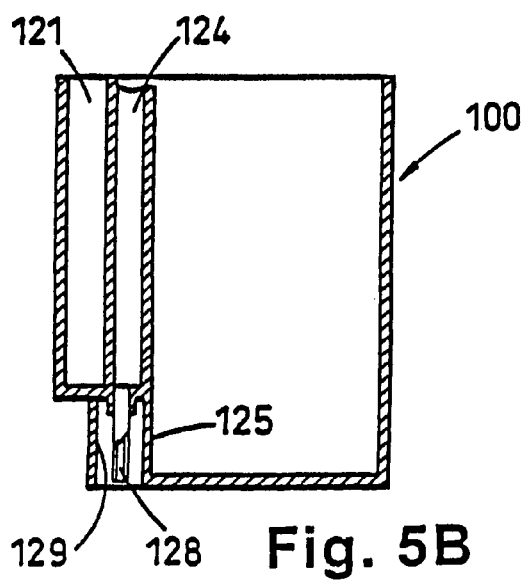
Figure 5E:
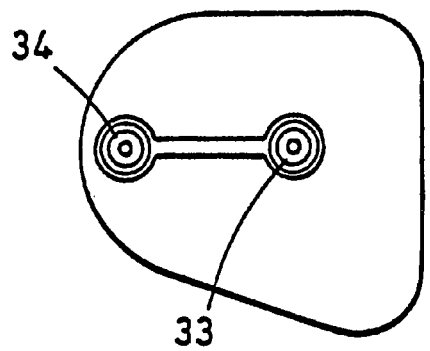
Figure 5C:
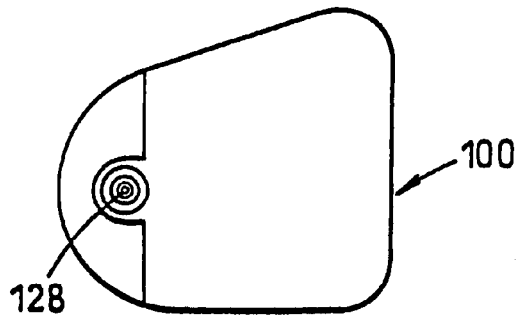
Figure 5F:
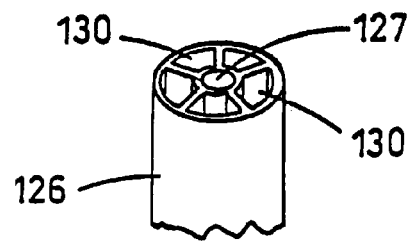

FIG. 5E is a plan view of the top of a preferred shape of canister, the generally triangular shape in section being chosen to fit better the space within cavity 20 (see FIG. 4). Tubular protrusions on the top of the canister are connected internally of the canister with respectively conduits 124 and 121 (see sectional view of FIG. 5B), thus maintaining a separation between the tubes which are represented by lines 103 and 106 in FIG. 1. At the base of the canister, a moulding 125 facilitates connection to a multi-partitioned tube 126 shown in FIG. 5F. Tube 126 has a central bore 127 which is sized to fit over a spigot 128 in moulding 125. At the same time, the external wall of tube 126 seals against the inner wall 129 of moulding 125. Thus, compartment 124 will connect with central bore 127 and the compartment 121 will connect with the annular spaces 130 of tube 126. In this way, a conduit 130 corresponds with line 106 and central bore 127 with line 101 as shown in FIG. 1.

The partitioned tube need not continue all the way to the wound site 102, but can be connected to a short section of single bore tube close to the wound site.

In the event of an air leak in the dressing at the wound site 102, this can be detected by both transducers 105 and 108 reading insufficient negative pressure for a specific time period and then triggering a leak alarm, i.e. a message on the LCD, preferably also with an audible warning.

Typically, the pump 6 is a diaphragm pump but other types of pumps and equivalent components to those specifically employed may be substituted.

Figure 7A:
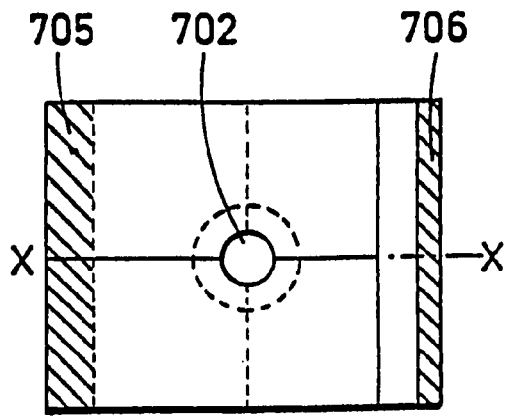
FIGS. 7A & 7B show a plan and perspective view of a surgical drape for use with the apparatus.
Figure 7B:
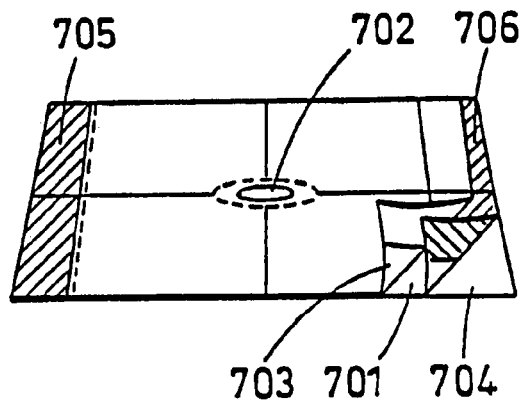

FIGS. 6A-6D show various views of a connector for attaching the multilumen tube at the wound site. FIGS. 7A and 7B show a plan and perspective view of a surgical drape for attaching the connector to a porous dressing at the wound site. The connector comprises a moulded plastics disc-like cup 601 having a centrally positioned spout 602. The spout 602 is sized to accept, as a closely sliding fit, the end of a multi-lumen tube e.g. of the kind shown in FIG. 5F or 6E.

In use, a porous dressing is cut to correspond with the extent of the wound and pressed onto the wound as shown in FIG. 10 of our above cited PCT application WO 96/05873. Instead of introducing the lumen into the foam dressing, the cup 601 is pressed onto the porous dressing and secured by a surgical drape. However, if desired, the end of the lumen can be passed into the spout and additionally pressed into the foam. A surgical drape such as shown in FIGS. 7A and 7B, can be used to secure the connector, lumen and dressing. The drape comprises a polyurethane film 701 coated on one side with a pressure-sensitive acrylic resin adhesive. A hole 702 is cut through all layers of the drape and the hole is dimensioned to correspond approximately with the outer cross-section of the spout 602. Film 701 has an overall size which allows it to be adhered to the patient's skin around the wound site, while at the same time, securing the connector to the porous dressing. A sufficient overlap around the wound is provided so that an airtight cavity is formed around the wound.

In an alternative form, the drape can be made in two parts, e.g. by cutting along the line X-X in FIG. 7A. With this arrangement, the wound can be sealed by overlapping two pieces of surgical drape so that they overlap each other along a line Y-Y as shown in FIG. 6D.

The surgical drape may include a protective film 703, e.g. of polyethylene, and a liner 704 which is stripped off prior to use to expose the pressure-sensitive adhesive layer. The polyurethane film may also include handling bars 705,706, which are not coated with adhesive, to facilitate stretching of the film over the wound site. The dressing is preferably a pad of porous, flexible plastics foam, e.g.

reticulated, open intercommunicating cellular flexible polyurethane foam, especially of the kind described in the above-mentioned PCT application WO 96/05873.

Alternatively, a reticulated intercommunicating cellular foam made from flexible polyvinylacetate or polyvinylalcohol foam may be used. The latter is advantageous because it is hydrophilic. Other hydrophilic open celled foams may be used.

In another method of therapy, the foam dressing may be sutured into a wound after surgery and the foam dressing connected to the pump unit by the multi-lumen catheter. Negative pressure can then be applied continuously or intermittently for a period determined by the surgeon, e.g. from about 6 hours to 4 to 5 days. After this period, the dressing is removed and the wound re-sutured.

This therapy improves the rate of granulation and healing of wounds after surgery.

We claim:

1. A reduced pressure treatment apparatus for administering reduced pressure to a wound site, the apparatus comprising:
    a drape for positioning over the wound site to create and maintain a substantially air-tight cavity between the wound site and the drape;
    a multi-lumen suction tube configured to be attached to a reduced pressure source, the multi-lumen suction tube having a center lumen and at least one outer lumen and being configured to deliver reduced pressure beneath the drape to the substantially air-tight cavity, the at least one outer lumen in fluid communication with the substantially air-tight cavity such that the reduced pressure is monitorable at the wound site through the at least one outer lumen; and
    wherein the multi-lumen suction tube is adapted to allow fluid to be drawn from the wound site through the center lumen, wherein the center lumen of the multi-lumen tube comprises a central bore adapted to remove fluids from the wound site and the at least one outer lumen comprises conduits located within the walls of the multi-lumen suction tube and adapted to allow air to flow there through, and wherein the conduits are circumferentially spaced at 90 degree intervals around the central bore.

2. The apparatus of claim 1 further comprising a pressure sensor operably connected to the at least one outer lumen of the multi-lumen suction tube.

3. The apparatus of claim 1 further comprising a pressure relief valve fluidly connected to the at least one outer lumen to enable administration of intermittent reduced pressure to the wound site.

4. The apparatus of claim 1 further comprising a connector operably associated with the drape and connectable to the multi-lumen suction tube to facilitate introduction of the reduced pressure to the substantially air-tight cavity, the connector having a spout for connection to an end of the multi-lumen suction tube.

5. The apparatus of claim 4, wherein the drape includes an aperture for the projection there through of the spout.

6. The apparatus of claim 1, wherein the drape is a plastic film.

7. The apparatus of claim 1, wherein the drape is coated with a pressure-sensitive adhesive for securing the drape over the wound site.

8. The apparatus of claim 1, wherein the at least one outer lumen is defined by annular spaces of the multi-lumen suction tube adapted to allow air to flow there through.

9. A reduced pressure treatment apparatus comprising:
    a manifold for distributing reduced pressure to a wound site;
    a drape for positioning over the manifold;
    a multi-lumen suction tube fluidly connected to the manifold, the multi-lumen suction tube having a center lumen to allow fluid to be drawn from the wound site and at least one outer lumen in fluid communication with the wound site such that the reduced pressure is monitorable at the wound site through the at least one outer lumen; and
    wherein the center lumen of the multi-lumen suction tube comprises a central bore adapted to remove fluids from the wound site and the at least one outer lumen comprises conduits located within the walls of the multi-lumen suction tube and adapted to allow air to flow there through, and wherein the conduits are circumferentially spaced at 90 degree intervals around the central bore.

10. The apparatus of claim 9 further comprising a pressure sensor operably connected to the at least one outer lumen of the multi-lumen suction tube.

11. The apparatus of claim 9 further comprising a pressure relief valve fluidly connected to the at least one outer lumen to enable administration of intermittent reduced pressure to the wound site.

12. The apparatus of claim 9, wherein the manifold is a polyvinyl alcohol foam.

13. The apparatus of claim 9, wherein the manifold is a polyurethane foam.

14. The apparatus of claim 9, wherein the multi-lumen suction tube is fluidly connected to the manifold by a connector to facilitate introduction of the reduced pressure to the manifold, the connector including a disc-like member having a lower face in contact with the manifold and a spout opposite said lower face for connection to an end of the multi-lumen suction tube.

15. The apparatus of claim 14, wherein the drape includes an aperture for the projection there through of the spout.

16. The apparatus of claim 9, wherein the drape is a plastic film.

17. The apparatus of claim 9, wherein the drape is coated with a pressure-sensitive adhesive for securing the drape over the manifold.

18. The apparatus of claim 9, wherein the at least one outer lumen is defined by annular spaces of the multi-lumen tube adapted to allow air to flow there through.

19. A reduced pressure treatment apparatus for administering reduced pressure to a wound site, the apparatus comprising:
   a manifold for distributing reduced pressure to the wound site;
   a multi-lumen suction tube fluidly connected to the manifold to deliver reduced pressure to the manifold, the multi-lumen suction tube having a center lumen and at least one outer lumen, the at least one outer lumen in fluid communication with the manifold such that the reduced pressure is monitorable at the wound site through the at least one outer lumen; and
   wherein the multi-lumen suction tube is adapted to allow fluid to be drawn from the wound site through the center lumen; and
   wherein the center lumen of the multi-lumen suction tube comprises a central bore adapted to remove fluids from the wound site, and the at least one outer lumen includes conduits located within the walls of the multi-lumen suction tube adapted to allow air to flow there through, and wherein the conduits are circumferentially spaced at 90 degree intervals around the central bore.

20. The apparatus of claim 19 further comprising a pressure sensor operably connected to the at least one outer lumen of the multi-lumen suction tube.

21. The apparatus of claim 19 further comprising a pressure relief valve fluidly connected to the at least one outer lumen to enable administration of intermittent reduced pressure to the wound site.

22. The apparatus of claim 19, wherein the wound site is a surface wound.

23. The apparatus of claim 19, wherein the manifold is a polyvinyl alcohol foam.

24. The apparatus of claim 19, wherein the manifold is a polyurethane foam.

25. The apparatus of claim 19, wherein the multi-lumen suction tube is fluidly connected to the manifold by a connector to facilitate introduction of the reduced pressure to the manifold, the connector including a disc-like member having a lower face in contact with the manifold and a spout opposite said lower face for connection to an end of the multi-lumen suction tube.

26. The apparatus of claim 25, wherein the drape includes an aperture for the projection there through of the spout.

27. The apparatus of claim 19, wherein the drape is a plastic film.

28. The apparatus of claim 19, wherein the drape is coated with a pressure-sensitive adhesive for securing the drape over the manifold.

29. The apparatus of claim 19, wherein the center lumen of the multi-lumen tube comprises a central bore adapted to remove fluids from the wound site and the at least one outer lumen is defined by annular spaces of the multilumen tube adapted to allow air to flow there through.

* * * * *

UNITED STATES PATENT AND TRADEMARK OFFICE
CERTIFICATE OF CORRECTION

| | | |
|---|---|---|
| PATENT NO. | : 7,670,323 B2 | Page 1 of 1 |
| APPLICATION NO. | : 11/713485 | |
| DATED | : March 2, 2010 | |
| INVENTOR(S) | : Kenneth William Hunt and Keith Patrick Heaton | |

It is certified that error appears in the above-identified patent and that said Letters Patent is hereby corrected as shown below:

On the Title page, Item (63), under Related U.S. Application Data, that portion of the priority claim reading "6,142,982." should be changed to --6,142,982, which is a continuation of International Application No. PCT/GB96/02802, filed on Nov. 14, 1996.--

On the Title Pg Item (30), under Foreign Application Priority Data, insert:

--November 14, 1995   (GB)  ............................ 9523253.4--

Signed and Sealed this

Fifth Day of October, 2010

David J. Kappos
*Director of the United States Patent and Trademark Office*